(12) United States Patent
Ruskin et al.

(10) Patent No.: US 11,690,550 B2
(45) Date of Patent: Jul. 4, 2023

(54) SYSTEM AND METHOD FOR AN INGESTIBLE PHYSIOLOGICAL MONITOR

(71) Applicant: THE GENERAL HOSPITAL CORPORATION, Boston, MA (US)

(72) Inventors: Jeremy Ruskin, Watertown, MA (US); Benjamin Pless, Brookline, MA (US)

(73) Assignee: The General Hospital Corporation, Boston, MA (US)

( * ) Notice: Subject to any disclaimer, the term of this patent is extended or adjusted under 35 U.S.C. 154(b) by 501 days.

(21) Appl. No.: 16/633,100

(22) PCT Filed: Jul. 20, 2018

(86) PCT No.: PCT/US2018/043925
§ 371 (c)(1),
(2) Date: Jan. 22, 2020

(87) PCT Pub. No.: WO2019/023473
PCT Pub. Date: Jan. 31, 2019

(65) Prior Publication Data
US 2020/0229725 A1    Jul. 23, 2020

Related U.S. Application Data

(60) Provisional application No. 62/537,137, filed on Jul. 26, 2017.

(51) Int. Cl.
*A61B 5/00*    (2006.01)
*A61B 5/285*   (2021.01)
(Continued)

(52) U.S. Cl.
CPC .......... *A61B 5/285* (2021.01); *A61B 5/02055* (2013.01); *A61B 5/0537* (2013.01);
(Continued)

(58) Field of Classification Search
CPC ..................................................... A61B 5/285
See application file for complete search history.

(56) References Cited

U.S. PATENT DOCUMENTS 10,149,635 B2    12/2018    Swiston
2003/0018280 A1   1/2003    Lewkowicz
(Continued)

FOREIGN PATENT DOCUMENTS

| | | |
|---|---|---|
| CN | 102159134 A | 8/2011 |
| CN | 110573062 A | 12/2019 |
| JP | 2009240474 A | 10/2009 |

OTHER PUBLICATIONS

International Searching Authority, International Search Report and Written Opinion for application PCT/US2018/043925, dated Oct. 12, 2018.
(Continued)

*Primary Examiner* — Joseph M Santos Rodriguez
(74) *Attorney, Agent, or Firm* — Quarles and Brady

(57) ABSTRACT

In accordance with some non-limiting examples of the disclosed subject matter, an ingestible system configured to acquire physiological information from an interior of a subject is provided, comprising a substrate and at least one physiological sensor. The at least one "physiological sensor can be coupled to the substrate and configured to capture physiological data from at least one of an internal area or an orientation in a digestive tract of the subject. The system can include a controller coupled to the substrate and configured to receive the physiological data and prepare the physiological data for one of transmission from the subject or analysis of the physiological data. The substrate, including the at least one physiological sensor and the controller coupled thereto can be configured to self-orient within the digestive tract of the subject, during ingestion of the system by the subject.

25 Claims, 9 Drawing Sheets

(51) Int. Cl.
*A61B 5/0205* (2006.01)
*A61B 5/0537* (2021.01)
*A61B 5/1455* (2006.01)
*A61B 5/361* (2021.01)
*A61B 5/07* (2006.01)
*A61B 5/024* (2006.01)
*A61B 5/08* (2006.01)

(52) U.S. Cl.
CPC .......... *A61B 5/073* (2013.01); *A61B 5/14552* (2013.01); *A61B 5/361* (2021.01); *A61B 5/42* (2013.01); *A61B 5/68* (2013.01); *A61B 5/746* (2013.01); *A61B 5/02444* (2013.01); *A61B 5/0809* (2013.01); *A61B 5/6873* (2013.01); *A61B 2562/0215* (2017.08); *A61B 2562/162* (2013.01)

(56) References Cited

U.S. PATENT DOCUMENTS

| | | |
|---|---|---|
| 2004/0106849 A1 | 6/2004 | Cho et al. |
| 2004/0186530 A1 | 9/2004 | Gluschuk |
| 2005/0027178 A1 | 2/2005 | Iddan |
| 2005/0183733 A1* | 8/2005 | Kawano ............. A61B 1/00156 607/116 |
| 2008/0194912 A1 | 8/2008 | Trovato |
| 2010/0021536 A1* | 1/2010 | Gross ..................... A61P 1/00 424/463 |
| 2010/0185055 A1 | 7/2010 | Robertson |
| 2010/0286660 A1 | 11/2010 | Gross |
| 2011/0054265 A1 | 3/2011 | Hafezi |
| 2011/0207998 A1 | 8/2011 | Katayama |
| 2012/0089122 A1 | 4/2012 | Lee et al. |
| 2015/0011874 A1 | 1/2015 | Amoako-Tuffour et al. |
| 2016/0000375 A1* | 1/2016 | Fürtsch et al. ....... A61B 5/1473 156/60 |
| 2016/0136104 A1* | 5/2016 | Niichel ............. A61K 41/0028 424/452 |

OTHER PUBLICATIONS

European Patent Office. Extended European Search Report for application 18838198.2 dated Mar. 29, 2021. 8 pages.

\* cited by examiner

SYSTEM AND METHOD FOR AN INGESTIBLE PHYSIOLOGICAL MONITOR

CROSS-REFERENCE TO RELATED APPLICATIONS

This application is based on, claims the benefit of, and claims priority to U.S. Provisional Application No. 62/537,137, filed Jul. 26, 2017, which is hereby incorporated by reference herein in its entirety for all purposes.

STATEMENT REGARDING FEDERALLY SPONSORED RESEARCH

N/A

BACKGROUND

Physiological monitoring is an important part of modern healthcare and is facing a continued growth in demand. Already, physiological monitoring is regularly used in relation to a variety of different clinical or non-clinical settings. For example, conventional Holter monitors are used to monitor or assist in the diagnosis of a variety of conditions, from atrial fibrillation (AF) to syncope. Recently, other wearable physiological monitors, including consumer electronics and even patches, have become prevalent for both medical and personal use.

Regarding prevalent cardiac diseases, AF remains a public health problem of epidemic proportions. Specifically, AF is associated with a fivefold increased risk for stroke, a twofold increased risk for congestive heart failure/death, and a 1.5 fold increased risk for cognitive impairment and dementia. Additionally, in many high risk patients, AF is episodic and is often asymptomatic. Thus, prolonged periods of cardiac monitoring may be required for detection and quantification of AF burden. The conventional Holter monitor can be used to perform such prolonged monitoring, but it is bulky and complex and, thereby, cumbersome to the patient and the caregivers.

With regard to physiological monitoring for sleep disorders, current practice forces a patient to attend a sleep study. For example, the patient is studied in a sleep lab for one or at most two nights, during a sleep study. Unfortunately, time spent at sleep labs can be at a substantial cost and inconvenience to the patient. When attempting to take such studies outside of the sleep lab, some monitoring components can be deployed into the home. However, such monitoring components are not intuitive for the patient to use independently and can interfere with sleep, be deployed improperly, and/or become disengaged during sleep. In these cases, the data that is collected may be impaired or unusable.

Accordingly, it would be desirable to have new systems, methods, and media for tracking physiological parameters for the volume and increasing diversity of physiological monitoring applications.

SUMMARY

The present disclosure provides systems and methods that overcome the aforementioned drawbacks. In accordance with some non-limiting examples of the disclosed subject matter, an ingestible system is provided that is configured to acquire physiological information from an interior of a subject. The system includes a substrate and at least one physiological sensor coupled to the substrate and configured to capture physiological data from at least one of an internal area or an orientation in a digestive tract of the subject. The system also includes a controller coupled to the substrate and configured to receive the physiological data and prepare the physiological data for one of transmission from the subject or analysis of the physiological data. The substrate, with the at least one physiological sensor and the controller coupled thereto, is configured to self-orient within the digestive tract of the subject during digestion of the system by the subject to orient the at least one physiological sensor in the at least one of the internal area or the orientation in the digestive tract of the subject.

In accordance with another non-limiting example of the disclosure, a method for internal monitoring is provided. The method includes ingesting an ingestible system. The ingestible system includes a capsule and a physiological monitor. The physiological monitor includes a substrate, at least one physiological sensor coupled to the substrate, and a controller coupled to the substrate and configured to receive the physiological data and prepare the physiological data for one of transmission from the subject or analysis of the physiological data. The substrate is folded and placed in the capsule to be ingested by a subject. The method further includes dissolving the capsule in a portion of an intestine of the subject and releasing the folded physiological monitor in the portion of the intestine and unfolding the folded physiological monitor in the portion of the intestine.

BRIEF DESCRIPTIONS OF THE DRAWINGS

DETAILED DESCRIPTION

Figure 1:
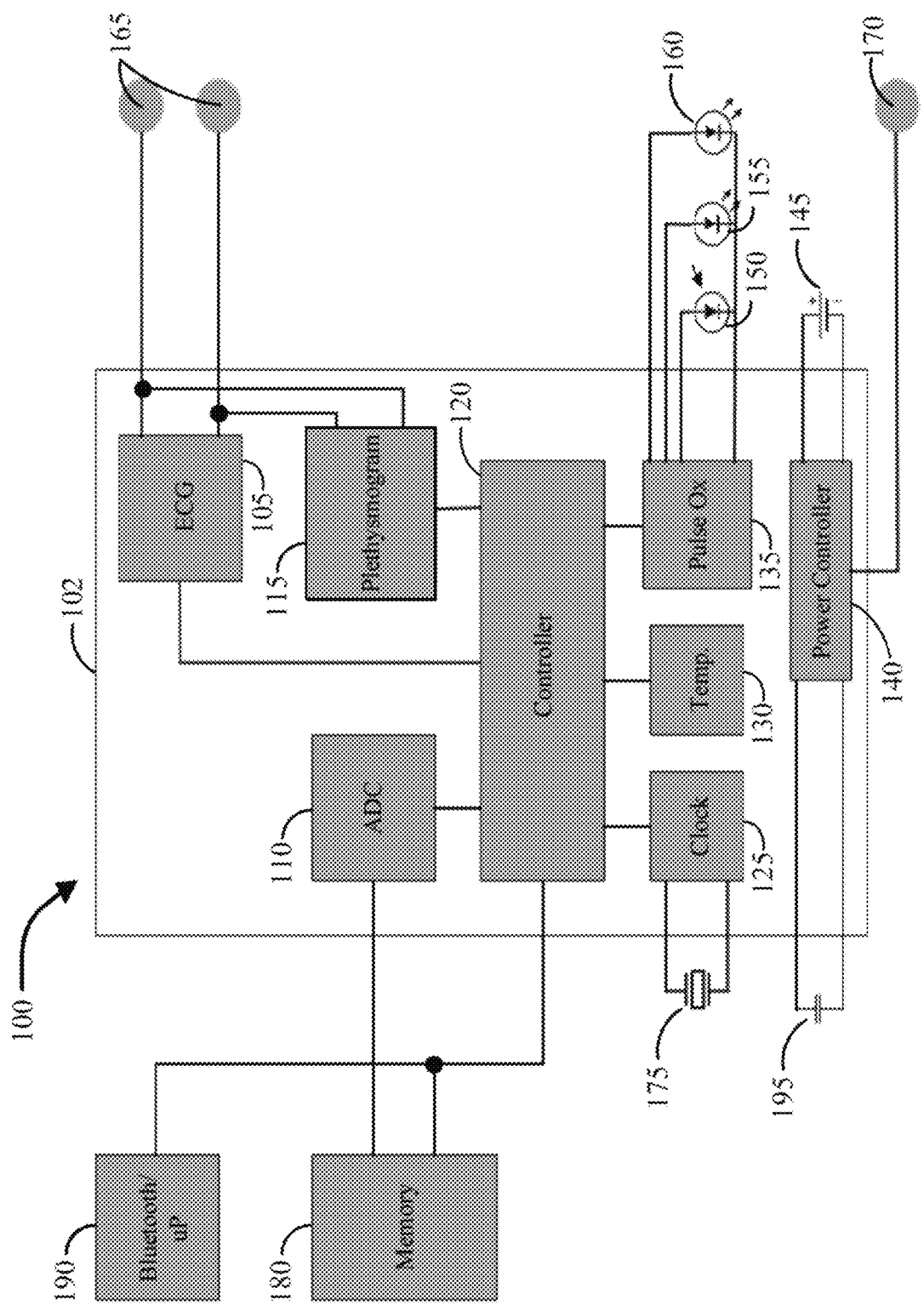
FIG. 1 is a block diagram of an ingestible physiological monitor, in accordance with some non-limiting examples of the disclosed subject matter.

In accordance with various non-limiting examples, mechanisms (which can, for example, include systems, methods, and media) for capturing, analyzing, and transmitting various physiological parameters using an ingestible monitor are described herein. In accordance with various non-limiting examples, an ingestible platform can combine the benefits of wearables and implantable loop recorders in a user-friendly and unobtrusive physiologic monitoring technology.

In some non-limiting examples, the ingestible platform can provide a simple, unobtrusive, and convenient method with which to monitor at-risk patients. Additionally or alternately, the ingestible platform can detect and quantify a variety of conditions. As will be described, the type of conditions for which the systems and methods of the present disclosure can be used to monitor are broad and diverse. To illustrate that breadth and diversity, two non-limiting examples of disparate conditions will be utilized: atrial fibrillation (AF) and sleep studies. These non-limiting examples are provided to illustrate the breadth of diversity of conditions, as well as clinical and non-clinical settings, for which the systems and methods provided herein can be used. These are but examples and neither AF nor sleep applications should limit the scope of the present disclosure.

The platform can be used to detect and/or quantify cardiac conditions, such as AF, leading to appropriate treatment (e.g., anticoagulation for stroke prophylaxis). Thus, in this way and others, the ingestible platform can improve patient outcomes. In some non-limiting examples, the ingestible platform may also facilitate decisions about the need for long term anticoagulation therapy in some patient cohorts with known AF (e.g. patients who have undergone catheter ablation or pharmacological therapy for suppression of AF).

In some non-limiting examples, the ingestible platform offers the potential for simple, convenient home monitoring of sleep patterns over longer periods of time, as well as follow-up monitoring after initiation of therapeutic interventions such as continuous positive airway pressure (CPAP).

In accordance with some non-limiting examples, the terms "processor" and "controller" can include one or more processors, memories, and/or programmable hardware elements. Additionally, the terms "processor" and "controller" are intended to include any types of processors, CPUs, microcontrollers, digital signal processors, and the like.

In accordance with some non-limiting examples, the terms "self-align" and "self-orient" can be used interchangeably. In some non-limiting examples the terms "self-align" and "self-orient" can refer to a first physical structure moving with relation to another physical structure. In some non-limiting examples the movement with relation to the first and second physical structure can include translation, or rotation, or any combination of translation or rotation between the first and second physical structure. In some non-limiting examples, the first physical structure or the second physical structure can be stationary. In some non-limiting examples, the first physical structure or the second physical structure is an internal portion of a subject. In some non-limiting examples, the internal portion of the subject includes a section of intestine. In some non-limiting examples, the first physical structure or the second physical structure can be an ingestible physiological monitor (e.g., the ingestible physiological monitor 100). In some non-limiting examples, "self-align" and "self-orient" can refer to a first surface of the first physical structure moving with relation to a second surface of the second physical structure, where moving can include any combination of translation or rotations of either the first or second surface. For example, in some non-limiting examples, "self-align" and "self-orient" can include a first surface of the ingestible physiological monitor translating and rotating such that the first surface of the ingestible physiological monitor faces the second surface of the second physical structure (e.g., the section of intestine).

FIG. 1 is a schematic diagram of an example of an ingestible physiological monitor 100, in accordance with some non-limiting examples of the subject matter. In some non-limiting examples, the ingestible physiological monitor 100 can include hardware and/or software that can be used to implement capturing, analyzing, and transmitting various physiological parameters, in accordance with some non-limiting examples of the subject matter. The physiological monitor can be arranged in a housing, container, or capsule 101. In some non-limiting examples, the device can contain a small, folded, electronic circuit housed in the housing (e.g., a gelatin capsule). The housing 101 is designed to be swallowed, passing through the stomach, and may even dissolve in the intestine. In some non-limiting examples, a dissolved capsule releases the circuit into the intestines. In such non-limiting examples, once the capsule dissolves, the substrate which is coupled to the circuit can unfold and retract to its original shape or structure. In some non-limiting examples, the substrate can be coated with a mucoadhesive on at least a portion of the top layer, the bottom layer, or combinations thereof. In some non-limiting examples, the layer in which includes integral physiological components (e.g., sensing electrodes 165) has a portion of the layer coated with a mucoadhesive. In some non-limiting examples, the layer opposite the mucoadhesive coated layer, includes one or more coatings designed to reduce or eliminate fluid flow friction. In some non-limiting examples, once the substrate retracts to its original shape, the ingestible physiological monitor 100 can travel in a randomized pattern, within the intestine. In some non-limiting examples, the ingestible physiological monitor 100 can move in a predictable pattern within the intestine. In some non-limiting examples, the layer containing the integral physiological components, and preferable containing the mucoadheive, contacts the lining of the intestine. In some non-limiting examples, upon contacting the lining of the intestine, the ingestible physiological monitor 100 can adhere to the mucosal layer of the intestine. In some non-limiting examples, once the ingestible physiological monitor 100 adheres to the wall of the intestine, any number of the integral physiological components can also contact the wall of the intestine. In some non-limiting examples, the circuit components that do not include the physiological sensors, can be adhered to the layer opposite the mucoadhesive coated layer, and preferably coated with a material to reduce or eliminate fluid flow friction. The adhered circuit can capture, analyze, and transmit various physiological parameters (e.g., electrocardiogram (ECG) waveforms, pulse oximetry, respiratory monitoring, and central temperature), to an external device. In some non-limiting examples, mechanical links can be integrally formed on the substrate, separating groups of electrical components. In some non-limiting examples, the mechanical links can be designed of a biodegradable material. In some non-limiting examples, the mechanical links can include a biogalvanic material, such that when energized, the mechanical links corrode.

As shown in FIG. 1, in some non-limiting examples, the ingestible physiological monitor 100 can include a circuit 102 (which, as a non-limiting example, may be an application-specific custom integrated circuit (ASIC)), a memory 180, a wireless communications module 190, a reference electrode 170, sensing electrodes 165, a crystal oscillator 175, a bypass capacitor 195, a power source 145, an infrared light-emitting diode (LED) 155, a visible-wavelength LED 160 (red), or a photodiode 150, or a combination of these components. In some non-limiting examples, the memory 180 can include any suitable volatile memory, non-volatile memory, storage, or any suitable combination thereof. For example, the memory 180 can include random-access memory (RAM), static random-access memory (SRAM), read-only memory (ROM), electrically erasable programmable read-only memory (EEPROM), one or more flash drives, one or more hard disks, one or more solid state drives, one or more optical drives, etc. In some non-limiting examples, the memory 180 can have encoded thereon a computer program for controlling operation of the processor 182 of the wireless communications module 190. In some non-limiting examples, SRAM can be preferred within the memory 180 as SRAM consumes less power when compared to other memory types.

In some non-limiting examples, the wireless communications module 190 can include a processor 182 and a Bluetooth module 192. In some non-limiting examples, wireless communications module 190 can be electrically connected to memory 180. In some non-limiting examples, the processor 182 can be electrically connected to all components of the system, and can execute at least a portion of a computer program to capture, analyze, and/or transmit physiological parameters. In some non-limiting examples, the processor 182 can have the same or similar functionality as the controller 120. For example, the processor 182 can instruct the ECG module 105 to capture an ECG signal, output the signal to the analog to digital converter (ADC) 110, analyze the captured ECG signal, and store the pre-processed and/or post-processed physiological values in the memory 180. In some non-limiting examples, the processor 182 can be any suitable hardware processor or combination of processors such as a central processing unit (CPU), a graphics processing unit (GPU), a microprocessor unit (MPU), etc. in some non-limiting examples, the processor 182 can execute at least a portion of the computer program to capture, analyze, and/or transmit physiological parameters. In some non-limiting examples, the processor 182 can execute at least a portion of the computer program to store physiological parameters in the memory 180. In some non-limiting examples, the computer program can cause the processor 182 to execute at least a portion of a process 300 described below in connection with FIG. 7.

In some non-limiting examples, the Bluetooth module 192 can include any suitable hardware, firmware, and/or software for communicating over a Bluetooth connection with an external device. For example, the Bluetooth module 192 can include one or more transceivers, one or more communication chips and/or chip sets, etc. Additionally or alternatively, the Bluetooth module 192 can receive instructions from an external device to execute at least a portion of a computer program. In some non-limiting examples, the Bluetooth module 192 can transmit various types of data, such as physiological parameters, physiological analysis results, and/or alerts to an external device. In some non-limiting examples, the Bluetooth module 192 can include or can be substituted for various forms and types of wireless communication (e.g., a Wi-Fi connection, an ultrasound connection, a cellular connection, a radio-frequency connection, etc.), to an external device.

In some non-limiting examples, reference electrode 170 can be electrically connected to the power controller 140 of the circuit 102. Additionally or alternatively, reference electrode 170 can be electrically connected to the controller 120 of the circuit 102. In some non-limiting examples, the reference electrode 170 can be preferably connected to the power controller 140, as to help prevent the reference electrode 170 from capturing noise. In some non-limiting examples, reference electrode 170 can be used to generate a reference voltage signal. In some non-limiting examples, reference electrode 170 can be biased using any or various suitable direct current (DC) or alternating current (AC) voltages. In some non-limiting examples, reference electrode 170 can be biased at circuit ground. In some non-limiting examples, reference electrode 170 can be a polarizable electrode, a non-polarizable electrode, or any type in-between. In some non-limiting examples, a non-polarizable electrode (e.g., an Ag/AgCl electrode) is desired for reference electrode 170. In some non-limiting examples, reference electrode 170 can be made from thin film silver of, for example, about 20 microns thick. In some non-limiting examples, reference electrode 170 can be made of other materials such as conductive polymers, gold, platinum, titanium, titanium nitride, iridium oxide, and/or the like or combinations thereof.

In some non-limiting examples, the sensing electrodes 165 may be formed using two electrodes as illustrated. In this way, two, separate, identical, individual electrodes may be used. In some non-limiting examples, each individual electrode can be electrically connected to ECG module 105. Additionally or alternatively, the sensing electrodes 165, can be polarizable electrodes, or non-polarizable electrodes, or any type in-between. In some non-limiting examples, a non-polarizable electrode (e.g. an Ag/AgCl electrode) is desired for the sensing electrodes 165. In some non-limiting examples, the sensing electrodes 165 can be made from thin film silver, for example, about 20 microns thick. In some non-limiting examples, the sensing electrodes 165 can be made of other materials such as conductive polymers, gold, platinum, titanium, titanium nitride, and/or iridium oxide.

In some non-limiting examples, the crystal oscillator 175 and the clock 125 provide a consistent clock frequency. For example, the crystal oscillator 175 can contain a crystal 176 that has a precise, intrinsic, resonant frequency, causing the crystal oscillator to oscillate at the crystal 176's resonant frequency, providing a consistent clock frequency. In some non-limiting examples, the oscillation frequency, determined by the crystal 176, enables the clock 125 to ensure accurate time-keeping. In some non-limiting examples, the accurate tracking of time by real-time clock 125 can provide time-stamping events or data logs that can be stored in memory 180. In some non-limiting examples, the time-stamping events and/or data logs can include the time/date of physiological events or alerts.

In some non-limiting examples, the bypass capacitor 195 can be electrically connected to the power controller 140. In some non-limiting examples, the bypass capacitor 195 can reduce peak power capability requirements from the battery or other power source 145 when the ingestible physiological monitor 100 is turned on. Additionally or alternatively, the bypass capacitor can prevent AC noise from disrupting the DC voltage provided by the power controller 140.

In some non-limiting examples, the power source 145 can be electrically connected to the power controller 140. In some non-limiting examples, the power source 145 can include any suitable components for supplying power to the power controller 140. For example, the power source 145 can include an electrochemical battery (e.g., a lithium ion battery). In some non-limiting examples, the battery can include a coin cell.

In some non-limiting examples, the infrared LED 155 can be electrically connected to the pulse oximeter module 135. In some non-limiting examples, the infrared LED 155 provides the necessary infrared illumination required by the pulse oximeter module 135. In some non-limiting examples, the red LED 160 provides the necessary red light illumination required by the pulse oximeter module 135. In some non-limiting examples, the photodiode 150 captures the reflected light produced by the infrared LED 155 and/or the red LED 160. A person having ordinary skill in the art will appreciate that the photodiode 150 can be substituted for a device that has material properties that depend on the type and/or amount of illumination, such as a photoresistor, a phototransistor, or the like. Additionally or alternatively, the photodiode 150 can contain one or more photodiode components, each configured to absorb a specific wavelength of light, such as infrared light from the infrared LED 155, and/or visible red light from the red LED 160).

As shown in FIG. 1, in some non-limiting examples, the circuit 102 can include the ECG module 105, the ADC 110, the plethysmogram module 115, the controller 120, the clock 125, the temperature circuit 130, the pulse oximeter module 135, and the power controller 140. In this way, most of the functionality of the system can be integrated into the circuit 102. In some non-limiting examples, the controller 120 can be electrically connected to the ECG module 105, the ADC 110, the plethysmogram module 115, the clock 125, the temperature circuit 130, the pulse oximeter module 135, and the power controller 140. In some non-limiting examples, the controller 120 can include a microcontroller unit (MCU), or other similar hardware components. In some non-limiting examples, the controller 120 can execute at least a portion of a computer program to control functionality of the electrically connected units. In some non-limiting examples, the controller 120 utilizes the clock 125 and crystal oscillator 175 to execute instructions, as well as logging and time-stamping physiological parameters or other data, physiological analysis results, and/or alerts. In some non-limiting examples, the computer program can cause the controller 120 to execute at least a portion of a process 300 to be described below in connection with FIG. 7. In some non-limiting examples, power controller 120 can include a ground reference electrode. In some non-limiting examples, the ground reference electrode can provide a circuit ground reference location to the system (e.g., a zero DC bias).

In some non-limiting examples, the ADC 110 can be electrically connected to the ECG module 105, the plethysmogram module 115, the temperature circuit 130, the pulse oximeter module 135, and the clock 125, and the reference electrode 170. In some non-limiting examples, the ADC 110 can be housed within the controller 120, and electrically connected to the same components as the controller 120. In some non-limiting examples, the ADC 110 can be electrically connected to the memory 180. In some non-limiting examples, the controller 120 can instruct the ADC 110 to store data values captured from the ECG module 105, the plethysmogram module 115, the temperature circuit 130, and the pulse oximeter module 135. In some non-limiting examples, the ADC 110 converts the analog outputs from the various electrically connected components into digital values. In some non-limiting examples, the ADC 110's resolution and sampling rate can be optimized for the desired signals of interest, as indicated by the monitoring or clinical applications to be performed. In some non-limiting examples, the ADC 110 can have and utilize its own clock.

In some non-limiting examples, the ECG module 105 can capture an electrocardiogram signal from the sensing electrodes 165. For example, the ECG module 105 can compute the signal difference between the two sensing electrodes 165. In some non-limiting examples, the reference electrode 170 can be electrically connected to the ECG module 105 and be used to compute a desired ECG signal. The desired ECG signal can be amplified to a gain of, as a non-limiting example, 200. In some non-limiting examples, the ECG module 105 can include analog filters in order to capture the desired signals in the frequency range (e.g., 2 to 100 Hertz (Hz)). Additionally or alternatively, the ECG module 105 can include digital filters to omit undesirable signals, out of the desired frequency range (e.g., noise, or other non-ECG physiological signals). In some non-limiting examples, the controller 120 and/or the processor 182 can execute at least a portion of a computer program to digitally process the captured ECG signals. For example, the controller 120 and/or the processor 182 can execute digital signal processing algorithms on the ECG signal. In some non-limiting examples, the ECG module 105 can include a level shifter, such that the entire amplified ECG signal can be outputted to the ADC 110, and then to the controller 120, where the digitalized signal can be stored in memory 180.

In some non-limiting examples, the plethysmogram module 115 can inject a series of current pulses (e.g., at a frequency of 30 Hz and amplitude of 50 micro amperes (uA)) into the sensing electrodes 165. In some non-limiting examples, plethysmogram module 115 can have a separate pair of electrodes, rather than also utilizing the pair of sensing electrodes 165 described above, where the separate electrodes can be similar in composition to the above-described sensing electrodes 165. In some non-limiting examples, the current pulses are injected into one electrode of the sensing electrodes 165, and the voltage can be measured across the sensing electrodes 165, dependent on the amplitude of the injected current pulses. In some non-limiting examples, the plethysmogram module 115 can include a synchronous demodulator that constructs the impedance waveform, the impedance waveform can derive a respiration signal. In some non-limiting examples, the plethysmogram module 115 can include analog filters in order to capture the desired demodulated signals in the frequency range (e.g., 0.05 to 5 Hz). Additionally or alternatively, the plethysmogram module 115 can include digital filters to omit undesirable signals, out of the desired frequency range (e.g., noise, and non-respiratory physiological signals). In some non-limiting examples, the controller 120 and/or the processor 182 can execute at least a portion of a computer program to digitally process the captured respiration signal. For example, the controller 120 and/or the processor 182 can execute digital signal processing algorithms on the respiration signal. In some non-limiting examples, the plethysmogram module 115 can include a level shifter, such that the entire amplified respiration signal can be outputted to the ADC 110, and then to the controller 120, where the digitalized signal can be stored in memory 180.

In some non-limiting examples, the temperature circuit 130 can be electrically connected to the controller 120 and the ADC 110. In some non-limiting examples, the temperature circuit 130 can include any suitable temperature sensing element. For example, a temperature sensing element may include a thermistor, a thermocouple, and/or a temperature sensing diode. In some non-limiting examples, the temperature circuit 130 includes the necessary electrical components needed to capture and amplify the temperature signal. For example, a thermistor oriented circuit may comprise a wheatstone bridge in order to accurately capture the temperature signal or a solid-state integrated circuit such as a PTAT (proportional to absolute temperature) may be used. In some non-limiting examples, the controller 120 can instruct the ADC 110 to capture the temperature signal and send the data values to memory 180, the temperature signal indicating the surrounding temperature.

In some non-limiting examples, the pulse oximeter module 135 can be electrically connected to the controller 120, the ADC 110, the infrared LED 155, the red LED 160, and/or the photodiode 150. In some non-limiting examples, the controller 120 can instruct the infrared LED 155 to illuminate infrared light (e.g., approximately 910 nanometer (nm) light wavelength). In some non-limiting examples, the controller 120 can instruct the ADC 110 to capture the reflected infrared light by the photodiode 150, and store the values in memory 180. In some non-limiting examples, the controller 120 can instruct the red LED 160 to illuminate visible red light (e.g., approximately 660 nm light wavelength). In some non-limiting examples, the controller 120 can instruct the ADC 110 to capture the reflected red light by the photodiode 150, and store the values in memory 180. In some non-limiting examples, the ratio of the logarithm of the amount of reflected infrared light can be compared to the logarithm of the amount of the reflected red light. In some non-limiting examples, the ratio of the logarithm of each of the reflected infrared light and the red light, can be used to calculate a saturated oxygen ratio/percentage (SAO2). In some non-limiting examples, the SA02 value can be stored in memory 180.

In some non-limiting examples, the power controller 140 can be electrically connected to the components of the system. For example, the power controller can be electrically connected to the power source 145 and distribute power to components of the system in a controlled manner. In some non-limiting examples, the power controller 140 can produce a constant voltage to the system (e.g., a voltage regulator). In some non-limiting examples, power controller can produce a constant current to the system (e.g., a current regulator). In some non-limiting examples, power controller 140 can include a ground reference electrode. In some non-limiting examples, the ground reference electrode can provide a circuit ground reference location to the system (e.g., a zero DC bias).

In some non-limiting examples, other physiological sensors (e.g., an accelerometer, a microphone, or a pressure sensor) can be electrically connected to the ADC 110, controller 120, and/or power controller 140. In some non-limiting examples, the other physiological sensors can include analog, digital filters, and/or digital signal processing algorithms to isolate the signals of interest, and store the captured values in the memory 180. In some non-limiting examples, the electrical components can all be transitioned to an integrated circuit (e.g., circuit 102), in order to decrease the size of the device.

Figure 2:
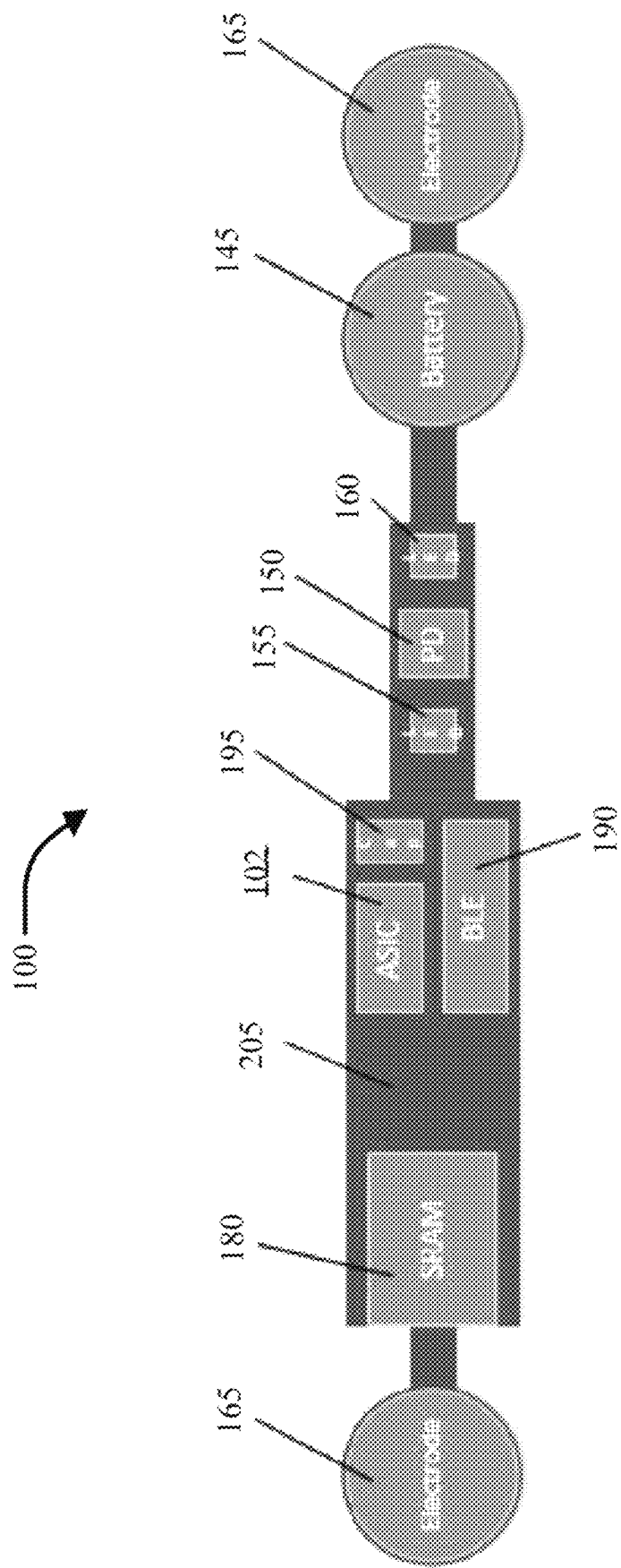
FIG. 2 is a top, plan view of an ingestible physiological monitor, in accordance with some non-limiting examples of the disclosed subject matter.

As shown in FIG. 2, in some non-limiting examples, the ingestible physiological monitor 100 can be constructed on a substrate 200. In some non-limiting examples, the ingestible physiological monitor 100 can be constructed on a substrate 200 that is not flexible. In some non-limiting examples, the substrate 200 can include be flexible. Also, the substrate 200 can include or be formed from a biodegradable material, such as silk, cellulose and/or other biocompatible and biodegradable materials. Additionally or alternatively, the substrate 200 can be chosen such that the substrate 200 decomposes after a predetermined amount of time or can be engineered to decompose upon an electrical command from the controller.

Figure 3:
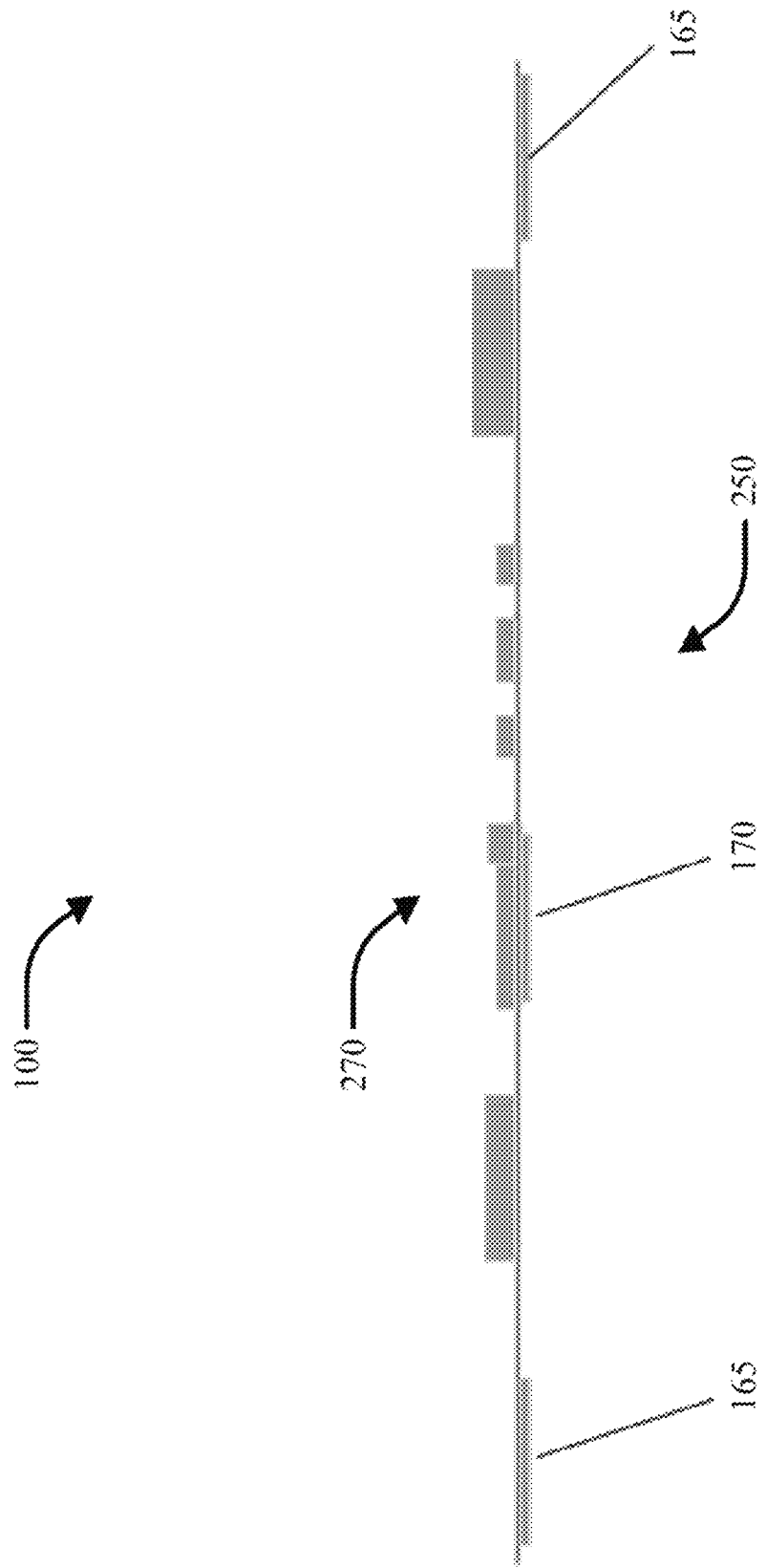
FIG. 3 is an example of side, elevation view of the ingestible physiological monitor of FIG. 2, in accordance with some non-limiting examples of the disclosed subject matter.

As shown in FIG. 3, the substrate 200 includes a bottom side 250 and a top side 270. The bottom side 250 and the top side 270 are arranged in opposition to one another. In some non-limiting examples, the sensing electrodes 165 can be disposed on the bottom side 250, and can be placed at either end of the assembly of the ingestible physiological monitor 100. In some non-limiting examples, a middle of the bottom side 250 of the ingestible physiological monitor 100 (e.g., shown in FIG. 3) can include the reference electrode 170. In some non-limiting examples, the other components, such as the memory 180, the wireless communications module 190, the bypass capacitor 195, the LEDs 155 and 160, and the photodiode 150 can be placed the top side 270 of the substrate. In some non-limiting examples, the power source 145 can include a battery 215 that supplies power to all components of the system. In some non-limiting examples, the infrared LED 155, the red LED 160, and/or the photodiode 150 can be directed through apertures (not shown) towards the bottom side 250, which can face the mucosa of the intestine. For example, the infrared LED 155 can emit infrared light through an infrared aperture 275, the infrared aperture 275 forming an opening through the substrate 200 to the bottom side 250. As another example, the red LED 160 can emit red light through a red light aperture 280, the red light aperture 280 forming an opening through the substrate 200 to the bottom side 250. Additionally or alternatively, the photodiode 150 can receive light through photodiode aperture 285, the photodiode aperture 285 forming an opening through the substrate 200 to the bottom side 250.

In some non-limiting examples, the top side 270 of the substrate 200 is coated with a thin hydrophobic coating. As one non-limiting example, the coating may include a 5 micron thick layer of parylene. In some non-limiting examples, the bottom side 250 can be completely coated or in part (e.g., only at one end, or with a pattern) with a mucoadhesive. For example, the mucoadhesive (which may include a hydrogel) can contain or can be largely formulated from a muco-adhesive such as poly(butadiene-maleic anhydride-co-L-DOPA) (PBMAD) or Carbopol. Additionally or alternatively, other suitable mucoadhesives can be used that are described in the literature.

As described above, in some non-limiting examples, the ingestible physiological monitor 100 can unfold in the intestine, where the mucoadhesive layer of bottom side 250 can adhere to the mucosa on the wall of the intestine. In some non-limiting examples, monitor 100 can be weighted or otherwise designed to self-align to position the top side 270 of the substrate 200 towards the lumen of the intestine. In some non-limiting examples, individual groups of components (e.g., the battery 215; the memory 255; the ASIC 102, the bypass capacitor 195, and the wireless communications module 190 as a group; the LEDs 155 and the sensing electrodes 165, and the photodiode 150 as another group) can be encapsulated 287. For example, the encapsulation 287 may be formed as a thin and conformal coat of a material like silicone or epoxy. The coating of the components can make the circuits biocompatible, and smooth so that contents of the intestine (e.g., chyme) can flow with minimal resistance over the top side 270 of ingestible physiological monitor 100.

Figure 4:
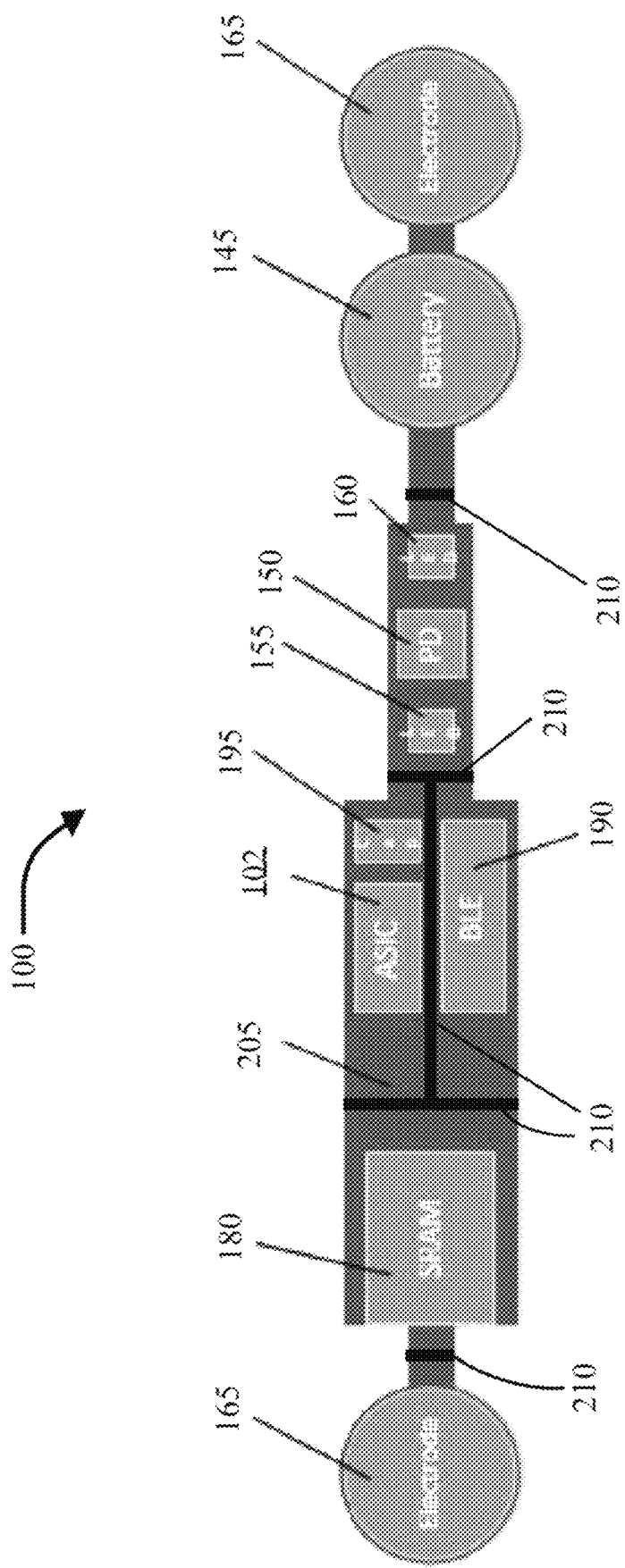
FIG. 4 is an example of a top, plan view of an ingestible physiological monitor that includes mechanical links between the components, in accordance with some non-limiting examples of the disclosed subject matter.

As shown in FIG. 4, in some non-limiting examples, ingestible physiological monitor 100 can include conductors integrated into the substrate 200 that electrically connect the various components. In some non-limiting examples, the conductors (e.g., thin traces deposited on the substrate) may be made from a biodegradable material such as a magnesium alloy. In some non-limiting examples, the ingestible physiological monitor 100 can include integral mechanical links 210 within substrate 200 and between sections of the substrate 200. In some non-limiting examples the mechanical links 210 can surround circuit elements, connecting the circuit elements (e.g., ASIC 102) to the substrate 200. In some non-limiting examples, the mechanical links 210 can be made of a biodegradable material, the biodegradable material engineered to have a specific lifetime. For example, the mechanical links 210 can be engineered to be biostable for a period of time (e.g., 10 to 14 days) and then rapidly biodegrade. In some non-limiting examples, the mechanical links 210 can be made of a biogalvanic material, electrically connected to the power controller 140, controller 120, and/or the processor 182. In some non-limiting examples, the controller 120 can instruct the biogalvanic mechanical links 210 to be energized, initiating a breakdown of the biogalvanic mechanical links 210. In some non-limiting examples, the lifetime of the mechanical links can be predetermined and stored in memory 180. The controller 120 can instruct the biogalvanic mechanical links 210 to be energized (and broken down), once the predetermined amount of time has passed. In some non-limiting examples, the mechanical links 210 can connect and secure the electrical components (e.g., memory 180) to the substrate 200. For example, if the mechanical links 210 are broken down, the electrical components can be released, having lost the secured connection between the mechanical links 210 and the substrate 200. In some non-limiting examples, the substrate 200 having lost the electrical components, is exposed to the fluid environment in the intestine and can decompose.

Figure 5:
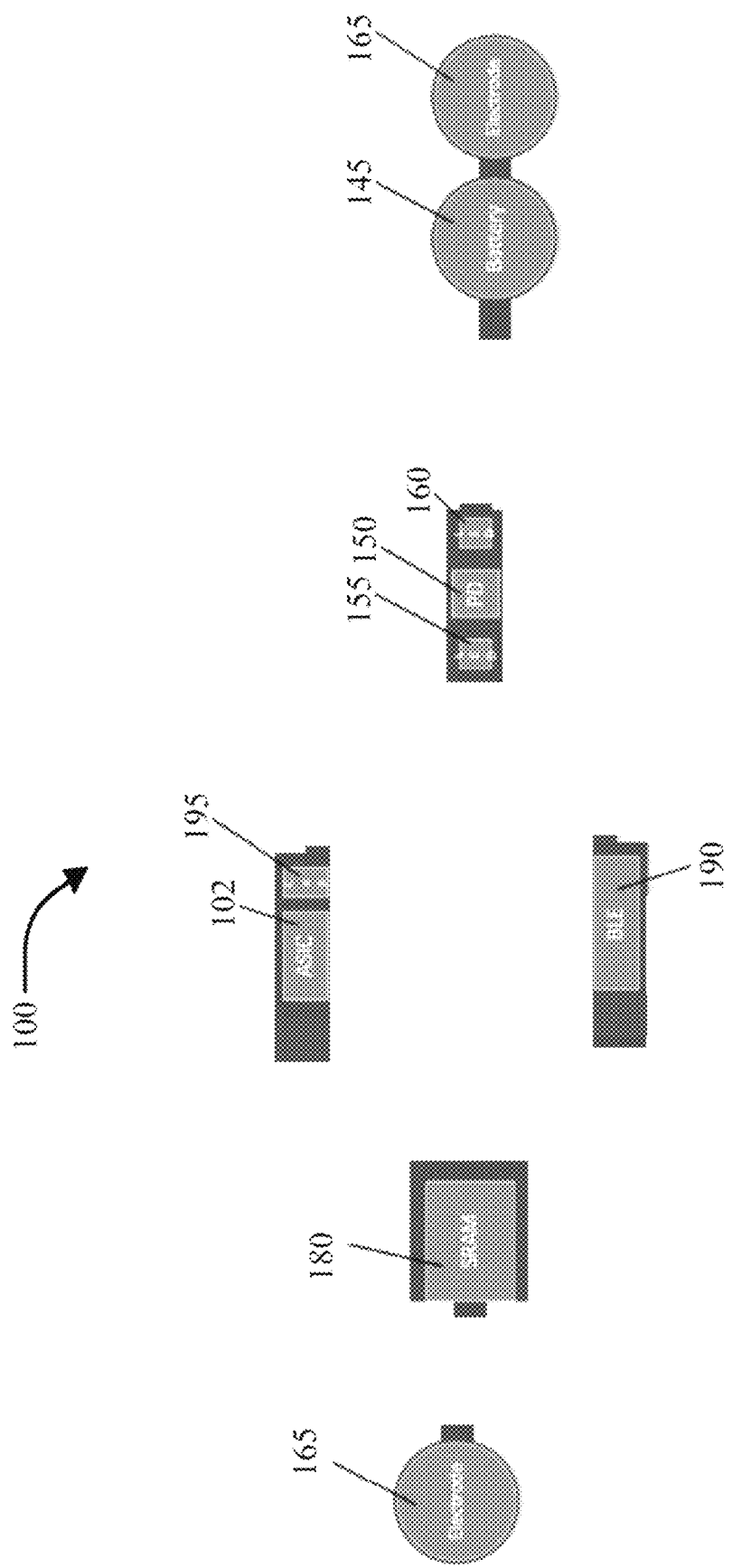
FIG. 5 is an example of a top, plan view of the ingestible physiological monitor of FIG. 4, where the mechanical links between components are removed, in accordance with some non-limiting examples of the disclosed subject matter.

FIG. 5, shows portions of the flexible substrate 200 that were connected by mechanical links 210. For example, after mechanical links 210 have been broken down and disappeared, the remaining portions of the flexible substrate 200 are exposed to the fluid in the lumen of the intestine causing the substrate to biodegrade releasing all components of the assembly into the lumen of the intestine.

Figure 6:
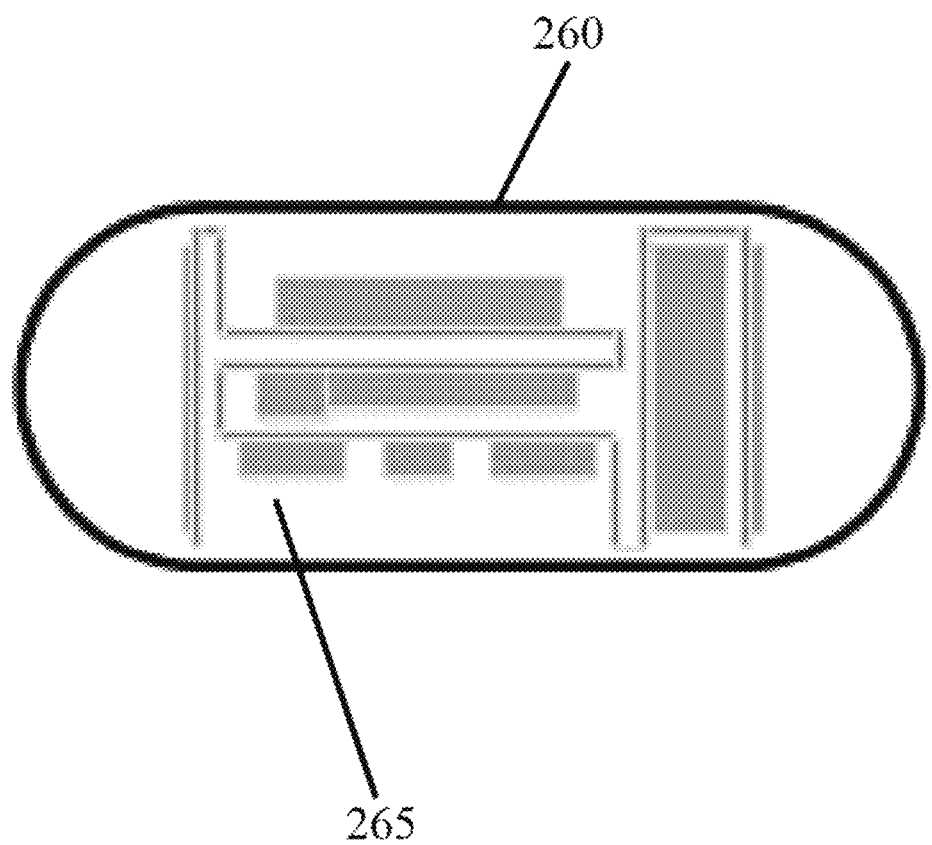
FIG. 6 is an example of a folded configuration of the ingestible physiological monitor, housed in an enteric coated capsule, in accordance with some non-limiting examples of the disclosed subject matter.

A shown in FIG. 6, in some non-limiting examples, the ingestible physiological monitor 100 can be folded between circuit elements into a compact shape 265, and the housing 101 of FIG. 1 can be formed as a capsule 260. In some non-limiting examples, the capsule 260 has an enteric coating. For example, the enteric coating can allow the capsule 260 containing a compact ingestible physiological monitor 100, to pass through the acidic (low pH) environment of the stomach, and dissolve in the neutral pH environment of the intestine.

Figure 7:
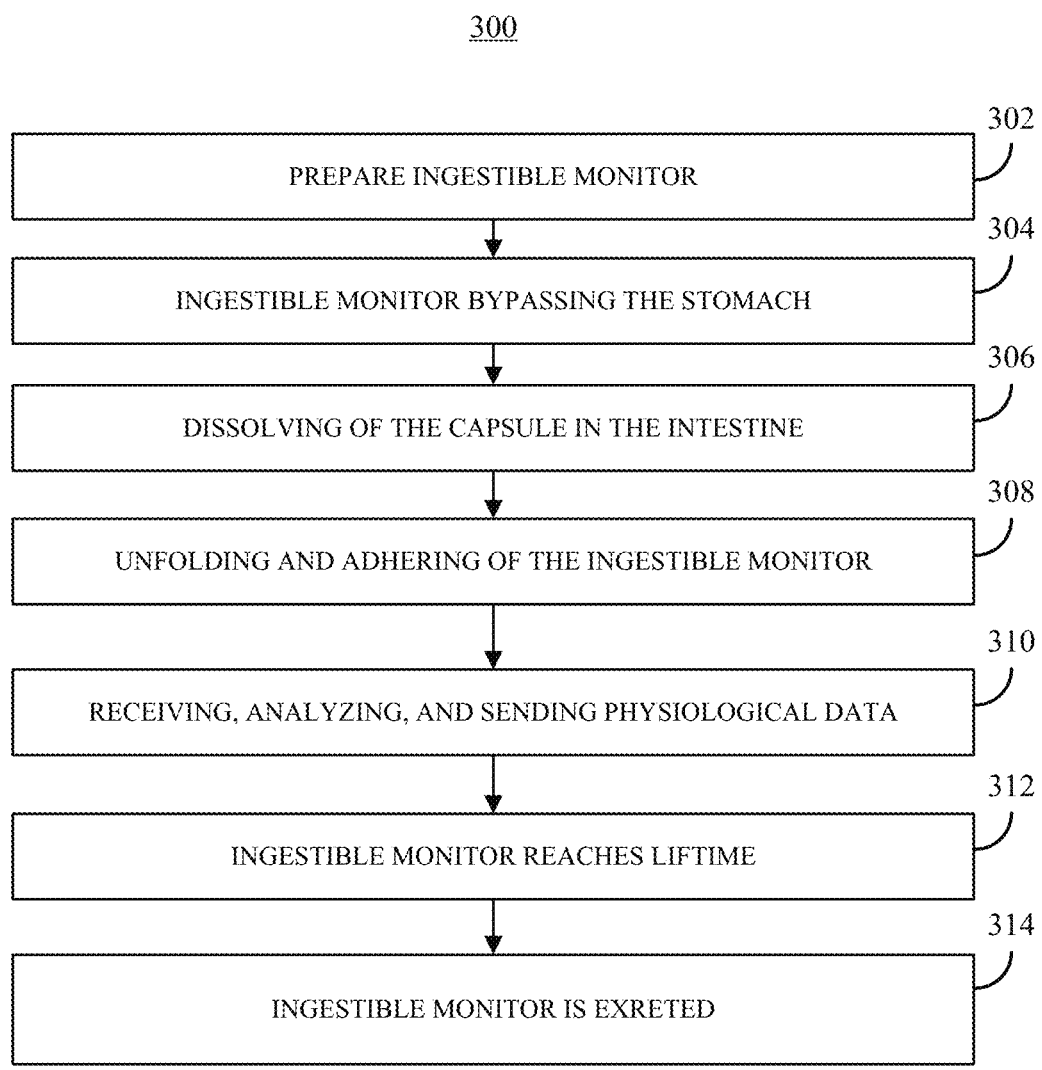
FIG. 7 is a flow chart setting forth some example steps of a process for capturing, analyzing, and transmitting various physiological parameters using an ingestible physiological monitor, in accordance with some non-limiting examples of the subject matter.

FIG. 7 shows an example of process 300 for capturing, analyzing, and transmitting various physiological parameters using an ingestible monitor. As described above, the ingestible physiological monitor 100 can be constructed on flexible substrate 200. In some non-limiting examples, the bottom side 250 of ingestible physiological monitor 100 can be coated with one or more mucoadhesives. Additionally or alternatively, the top side 270 of the ingestible physiological monitor 100 can be coated with a hydrophobic coating. In some non-limiting examples, the groups of components attached to a flexible substrate 200 can be coated in epoxy or silicone. The silicone, epoxy, and other hydrophobic coatings can allow for smooth flow of intestinal contents, which can decrease the fluid flow resistance between the top side 270 of the ingestible physiological monitor 100 and the intestinal contents. In some non-limiting examples, the ingestible physiological monitor 100 can be folded into a compact shape (e.g., compact shape 265 of FIG. 6) and placed into an enteric coated capsule. The flexible substrate 200 can allow the ingestible physiological monitor 100 to take on a range of compact shapes, and can allow the ingestible physiological monitor 100 to be placed in the capsule. In some non-limiting examples, it may be desirable to separate the electrical components using the compact shape 265. Additionally or alternatively, the sensing electrodes 165 can be separated in the capsule to different regions within the capsule. In some non-limiting examples, the sensing electrodes 165 can be in a dry environment in the capsule, and the plethysmogram module 115 can detect when the ingestible physiological monitor 100 remains in a dry environment in its compact shape 265. For example, when the sensing electrodes 165 are in a dry environment, the impedance measured across them by the plethysmogram module 115 is a high, non-physiological value. This high impedance value can indicate that the ingestible physiological monitor 100 remains in a dry environment in its compact shape 265. Once the ingestible physiological monitor 100 is placed in an enteric capsule, the capsule can be swallowed by the subject. In some non-limiting examples, the ingestible physiological monitor 100 can have a chosen predetermined location within an internal portion of the subject. For example, the type and or amount of mucoadhesive coating can allow the ingestible physiological monitor 100 to adhere to different portions within the small intestine (e.g., the duodenum, the jejunum, or the ileum). As another example, the physiological ingestible monitor 100 can be placed in a capsule 260 so as to dissolve in the stomach, and thus releasing the ingestible physiological monitor 100 in the stomach. In some non-limiting examples, the ingestible physiological monitor 100 can have a chosen predetermined orientation within an internal portion of the subject. For example, the side of substrate 200 (e.g., top side 270, or bottom side 250) that is coated with the mucoadhesive can determine the orientation of the ingestible physiological monitor 100 within the subject, as the side that contains the mucoadhesive can adhere to the wall of the intestine, while the side opposite faces the lumen. Additionally or alternately, the physiological sensor(s) 198 can be positioned on the ingestible physiological monitor 100 so as to benefit from the predetermined orientation and/or predetermined location of the ingestible physiological monitor 100. For example, the physiological sensor(s) 198 can be placed on a side of the substrate 200 (e.g., top side 270, or bottom side 250) that faces the intestinal lumen of the subject (opposite the mucoadhesive), the predetermined location being the intestines, and the predetermined orientation allowing the mucoadhesive coated side to face the wall of the intestine.

With the ingestible physiological monitor 100 prepared, the ingestible physiological monitor 100 can be consumed by a subject at 302. At 304, the ingestible physiological monitor 100, housed in an enteric capsule, passes the stomach. In some non-limiting examples, due to the enteric coating of the capsule, the capsule remains stable and does not dissolve in acidic environment (low pH) of the stomach. The capsule containing the ingestible physiological monitor 100, can exit the stomach, passing into the intestine.

At 306, the capsule containing the ingestible monitor 100 reaches the intestine and dissolves. In some non-limiting examples, the enteric coating of the capsule can allow the capsule to dissolve at a nearly neutral pH of the intestine. In some non-limiting examples, the dissolved capsule can release the ingestible physiological monitor 100 remaining in a compact shape 265.

At 308, the ingestible physiological monitor 100 unfolds from a compact shape 265. For example, the flexible substrate 200 flexes and stores strain energy while in the compact shape 265, where the capsule prevents unfolding of the flexible substrate 200. After the capsule dissolves and is removed, the flexible substrate 200 releases the stored strain energy, unfolding, and the ingestible physiological monitor 100 resumes its unfolded shape (e.g., as shown in FIG. 2). In some non-limiting examples, once the sensing electrodes 165 are exposed to fluids in the GI tract, the impedance measured by the plethysmogram module 115 circuit drops to within a comparatively low, physiological impedance range. Additionally or alternatively, this information may be used by the controller 120 to mark the time that the circuit unfurled and began to function in the body. In some non-limiting examples, the ingestible physiological monitor 100 can move in a randomized pattern within the intestine, and/or travel with the intestinal contents. In some non-limiting examples, the bottom side 250 of the ingestible physiological monitor 100 can be designed to contact the intestinal wall, where the mucoadhesive secures and allows the ingestible physiological monitor 100 to remain in contact with the wall. In some non-limiting examples, the ingestible physiological monitor 100 can be designed to contact the intestinal wall of the duodenum, the jejunum, or the ileum of the small intestine. In some non-limiting examples, the sensing electrodes 165 and reference electrode 170 can be designed to contact the intestinal wall.

At 310, the process 300 continues by the monitor 100 receiving, analyzing, and sending physiological data. In some non-limiting examples, once the ingestible physiologic monitor 100 is unfolded and adhered to the in the intestinal tract, the device can monitor ECG, respiration, saturated oxygen, plethysmogram and core temperature. In some non-limiting examples, the controller 120 can instruct the ECG module 105, the plethysmogram module 115, the pulse oximeter module 135, and the temperature circuit 130 to capture the corresponding signals discussed above. In some non-limiting examples, physiological events and corresponding logs can be stored in memory 180. For example the controller 120 can analyze the ECG signal for cardiac events (e.g., atrial fibrillation, bradyarrhythmias, atrial fibrillation (AF), and/or arrhythmias including but not limited to ventricular arrhythmias) using known algorithms. In some non-limiting examples, controller 120 can store the date and/or time of the cardiac events in memory 180.

In some non-limiting examples, the controller 120 can analyze the impedance data and/or waveform using known algorithms. For example, the controller 120, using the plethysmogram data and/or the impedance waveform, can detect respiratory events such as normal breathing, depressed respiration, apnea, or disordered breathing. The controller 120 can capture the date and/or time of the respiratory events, and can store these logged events in memory 180. In some non-limiting examples, the controller 120 can monitor the SAO2 of the subject using the pulse oximeter module 135. In some non-limiting examples, the controller 120 can detect changes in SAO2, in particular drops of 3% or greater, and store the date and/or time of these events in the memory 180. Additionally or alternatively, the pulse oximetry signal and/or the ECG signal may be analyzed by the controller 120 to derive a respiration signal. For example, the SAO2 signal alone can be used to create a respiration signal by detecting the pulsatile timing (e.g., time-varying peaks of the signal) of the SAO2 waveform. As another example, the ECG signal alone can be used to create a respiration signal by detecting the pulsatile timing (e.g., time-varying peaks of the signal such as timing of the QRS complex) of the ECG waveform. In some non-limiting examples, the SAO2 waveform can be preferably superimposed over the ECG waveform to derive the respiration signal. For example, the time and/or amplitude relationship between various time-varying peaks of the SAO2 waveform and ECG waveform indicate the respiration signal. In some non-limiting examples, the respiratory sinus arrhythmia (RSA) can be derived from any respiration signal (e.g., from the plethysmogram, the ECG, or the SAO2 signals). In some non-limiting examples, the derived respiration signal (e.g., from the ECG waveform and/or the SAO2 waveform) can be compared to the calculated respiration impedance waveform to ensure an accurate respiration signal has been captured. In some non-limiting examples, the temperature circuit 130 can be sampled by the controller 120 on a regular basis to capture the internal temperature of a subject, and store this value, along with a date and/or time in memory 180.

In some non-limiting examples, the controller 120 can combine respiration signals, SAO2, and optionally motion (from an accelerometer), in order to conduct sleep studies each night for as long as the ingestible physiological monitor 100 is resident in the patient (e.g., one night or up to one week). In some non-limiting examples, the controller 120 can detect sleep apnea during a sleep study. In some non-limiting examples, the ingestible physiological monitor 100 can transmit an alarm to an external device (e.g., the first external device 450 and/or the second external device 470) when the patient is in distress (e.g., over communication link 462, 482, and/or 484). For example, the controller 120 of the ingestible physiological monitor 100 can monitor respiration, heart rate, core temperature, and/or SAO2, in order to detect the presence of physiologic distress, when individual parameters or combinations of parameters meet predefined conditions. In a more particular example, rapid or depressed breathing, a high or low core temperature, and low SAO2 can trigger the ingestible physiological monitor 100 to transmit an emergency message to an external device (e.g., the first external device 450 and/or the second external device 470). In some non-limiting examples, the detected physiological distress can be related to anaphylactic shock, seizures, drug overdose, congestive heart failure, cardiac arrest, and/or other military and sports applications. In some non-limiting examples, the external device can be a smart phone carried by the patient, the smart phone providing an audible indicator and/or a visual indicator once the alarm has been received by the smart phone. In some non-limiting examples, the external device can relay the alarm (sent by the ingestible physiological monitor 100) that includes an emergency message to caregivers or clinicians. In some non-limiting examples, the relayed signal to the caregiver or clinicians, indicates the need for urgent intervention. In some non-limiting examples, the external device is a smart phone.

At 312, the process 300 includes the ingestible physiological monitor reaching a predetermined lifetime. In some non-limiting examples, prior to the folding and packaging of the ingestible physiological monitor 100, a predetermined lifetime can be stored in memory 180. For example, the predetermined lifetime can be an amount of time (e.g., days) or a specific date. In some non-limiting examples, the ingestible physiological monitor 100 can reside in the subject for one to four weeks. In some non-limiting examples, the ingestible physiological monitor 100 can be engineered to decompose at a predetermined time. For example, the flexible substrate 200 of the ingestible physiological monitor 100, can degrade after the predetermined amount of time. Additionally or alternatively, the flexible substrate 200 can include mechanical links 210 that can be engineered to degrade after a predetermined amount of time. In some non-limiting examples, the mechanical links 210 can include a biogalvanic material, such that upon activation of the mechanical links 210, they decompose. In some non-limiting examples, the plethysmogram module 115 can monitor the impedance across the sensing electrodes 165 and automatically detect when the device has unfurled. For example, when the impedance value measured across the sensing electrodes 165 changes from a high value (when dry in the capsule) to a physiological value, this indicates that the device has unfurled in a physiologic environment. The controller 120 can capture this date and/or time and store it in memory 180. In some non-limiting examples, this captured and stored date and/or time can be used as the activation time for the device. In some non-limiting examples, the capturing of the activation time by controller 120 causes, the predetermined time (e.g., days) to begin to countdown. In some non-limiting examples, once the predetermined time has been reached, the controller 120 can activate the mechanical links 210, which can be made of a biogalvanic material, to decompose. This causes the pieces of the ingestible physiological monitor 100 to separate at sections that were once connected by the mechanical links 210. For example, the mechanical links 210 can connect and secure the electrical components (e.g., memory 180) to the substrate 200. Additionally or alternatively, if the mechanical links 210 are broken down, the electrical components can be released, having lost the secured connection between the mechanical links 210 and the substrate 200. In some non-limiting examples, the substrate 200 having lost the electrical components, can remain attached to the intestine wall and can decompose.

At 314, process 300 ends with the ingestible physiological monitor 100 being excreted from the subject. In some non-limiting examples, once the ingestible physiological monitor separates in sections (e.g., from dissolving mechanical links 210), the pieces mix with the intestinal contents, and are excreted from the body. In some non-limiting examples, the pieces can include the circuit components. In some non-limiting examples, the pieces can include sections of the substrate, due to the decomposing of the integrally formed mechanical links 210. In some non-limiting examples, the flexible substrate 200 dissolves after a period of time, freeing the circuit components, and allowing the components to mix with the intestinal contents, to be excreted from the subject. In some non-limiting examples, after a period of time, the entire ingestible physiological monitor 100 can mix with the intestinal contents, to be excreted from the subject.

Figure 8:
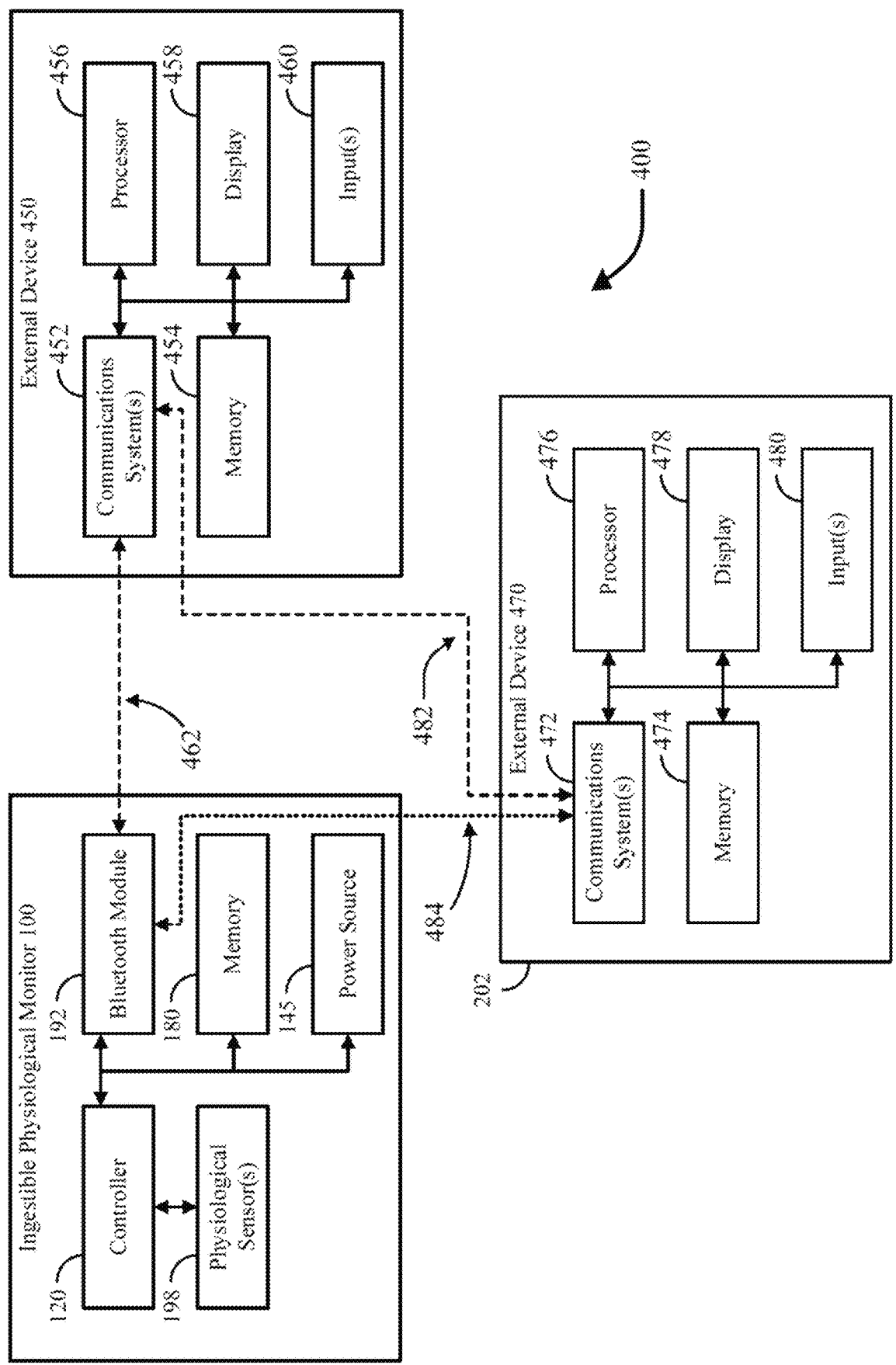
FIG. 8 is a block diagram for communicating between external devices and an ingestible physiological monitor, and/or the communication between external devices themselves, in accordance with some non-limiting examples of the subject matter.

As shown in FIG. 8, in some non-limiting examples, the first external device 450 can include a communications system(s) 452, memory 454, a processor 456, a display 458, and one or more inputs 460. In some non-limiting examples, the memory 454 can include any suitable storage device or devices that can be used to store instructions, values, etc., that can be used, for example, by the processor 456 to control the operation of ingestible physiological monitor 100, to communicate with the ingestible physiological monitor 100 via communications system(s) 452, etc. For example, the first external device 450 can instruct, via a communication system(s) 452 and the processor 456, the controller 120 to capture physiological data, via the physiological sensor(s) 198 and store the physiological values in the memory 180 or send the values, over a communication system(s) 452 to be stored in the memory 454 of the first external device 450. In some non-limiting examples, physiological sensor(s) 198 can include an ECG module, a plethysmogram, a pulse oximeter, a temperature circuit, an accelerometer, a pressure sensor, and/or a microphone.

FIG. 8 shows an example of the ingestible physiological monitor 100 in communication with the first external device 450, and the first external device 450 in communication with the second external device 470. In some non-limiting examples, the processor 456 of the first external device 450 can have functionality, components, and/or connections similar to components of the processor 476 of the second external device 470. In some non-limiting examples, the memory 454 of the first external device 450 can have functionality, components, and/or connections similar to the memory 474 of the second external device 470. In some non-limiting examples, the display 458 of the first external device 450 can have functionality, components, and/or connections similar to a display 478 of the second external device 470. In some non-limiting examples, input(s) 460 of the first external device 450 can have functionality, components, and/or connections similar to input(s) 480 of the second external device 470. In some non-limiting examples, the communications system(s) 452 of the first external device 450 can have functionality, components, and/or connections similar to a communication system(s) 472 of the second external device 470. In some non-limiting examples, the first external device 450 can be identical to the second external device 470.

In some non-limiting examples, the first external device 450 can instruct the ingestible physiological monitor 100 using the processor 456 and over the communication system(s) 452, to retrieve from the memory 180, previously stored physiological data values and/or physiological analyses, and send these physiological data values and/or physiological analyses to be stored in the memory 454, over the communication system(s) 452. The memory 454 can include any suitable volatile memory, non-volatile memory, storage, or any suitable combination thereof. For example, the memory 454 can include RAM, ROM, EEPROM, one or more flash drives, one or more hard disks, one or more solid state drives, one or more optical drives, etc. In some non-limiting examples, the memory 454 can have encoded thereon a computer program for controlling operation of the ingestible physiological monitor 100.

In some non-limiting examples, the processor 456 can be any suitable hardware processor or combination of processors, such as a central processing unit (CPU), a graphics processing unit (GPU), a microcontroller unit (MCU), a microprocessor unit (MPU), etc. In some non-limiting examples, the processor 456 can execute at least a portion of the computer program to receive physiological data or physiological analyses, from the ingestible physiological monitor 100. In some non-limiting examples, the receiving of physiological parameters and/or analyses can be implemented using the display 108 to present a graphical user interface (GUI) configured to receive user input, which can control the processor 456. In some non-limiting examples, physiological data values can be provided to the display 108. In some non-limiting examples, the computer program can cause the processor 456 to execute at least a portion of the process 300 described below in connection with FIG. 7.

In some non-limiting examples, the display 458 can include any suitable display devices, such as a computer monitor, a touchscreen, a television, etc. In some non-limiting examples, the input(s) 460 can include any suitable input devices and/or sensors that can be used to receive user input, such as a keyboard, a mouse, a touchscreen, a microphone (e.g., for receiving voice commands), etc.

In some non-limiting examples, the communications system(s) 452 can include any suitable hardware, firmware, and/or software for communicating with the ingestible physiological monitor 100, for communicating information over the communication link 462, and/or for communicating over any other suitable communication link (e.g., the communication link 482) and/or communication network(s). For example, the communications system(s) 452 can include one or more transceivers, one or more communication chips and/or chip sets, etc. In a more particular example, the communications system(s) 452 can include hardware, firmware and/or software that can be used to establish a coaxial connection, a fiber optic connection, an Ethernet connection, a USB connection, a Wi-Fi connection, a Bluetooth connection, a cellular connection, etc. In some non-limiting examples, the Bluetooth module 192 can communicate directly with the first external device (e.g., a smart phone) or other Bluetooth enabled devices outside the patient's body. A person having ordinary skill in the art will appreciate that other Bluetooth enabled devices can include various forms and types of wireless communication (e.g., a Wi-Fi connection, a cellular connection, a radio-frequency connection, etc.), such that the ingestible physiological monitor 100 can communicate with the first external device 450.

In some non-limiting examples, the first external device 450 can communicate with the second external device 470, over the communication link 482. In some non-limiting examples, the communications system(s) 472 can include any suitable hardware, firmware, and/or software for communicating with the second external device 470, for communicating information over the communication link 482, and/or for communicating over any other suitable communication link and/or communication network(s). For example, the communications system(s) 472 can include one or more transceivers, one or more communication chips and/or chip sets, etc. In a more particular example, the communications system(s) 472 can include hardware, firmware and/or software that can be used to establish a coaxial connection, a fiber optic connection, an Ethernet connection, a USB connection, a Wi-Fi connection, a Bluetooth connection, a cellular connection, etc. In some non-limiting examples, the communication link 482 can relay an alert, indicated initially by the the ingestible physiological monitor 100. For example, based on physiological data from the physiological sensor(s), the ingestible physiological monitor 100 can send an alert via the communications link 462 to the first external device 450 (e.g., a smartphone). In some non-limiting examples, upon receiving the alert, the first external device 450 can relay the alert to the second external device 470 (e.g., a smartphone, a computer, etc.) via the communications link 482. In some non-limiting examples, the second external device 470 can be owned by a health professional (e.g., a physician).

In some non-limiting examples, the communication link 484 (between communication system(s) 472 and the Bluetooth module 192) allows communication between the second external device 470 and the ingestible physiological monitor 100. In some non-limiting examples, the communication link 484 allows a physician to configure the ingestible physiological monitor 100. For example, the second external device 470 can instruct the ingestible physiological monitor 100 to collect certain types of physiological data. In some non-limiting examples, the second external device 470 can instruct the ingestible physiological monitor 100 to retrieve and send the collected physiological data over the communication link 484.

Figure 9:
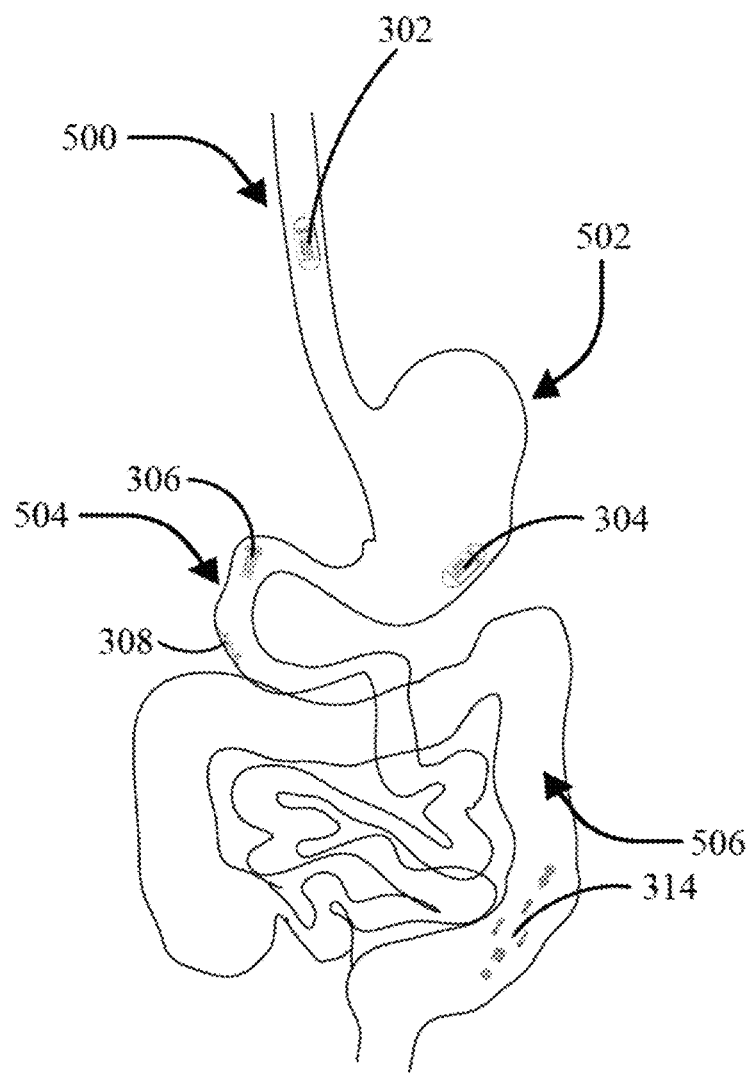
FIG. 9 is a schematic diagram illustrating an example of a process similarly or according to FIG. 7, for capturing, analyzing, and transmitting physiological parameters using an ingestible physiological monitor and showing anatomic features of a subject, in accordance with some non-limiting examples of the subject matter.

FIG. 9 shows illustrates an example of how the process 300 described above proceeds with respect to corresponding anatomy. In some non-limiting examples, the ingestible physiological monitor 100 can be folded into a compact shape 265 and housed in an enteric capsule, ingested, and passed through the esophagus 500, similarly or according to 302 of process 300. In some non-limiting examples, the enteric capsule housing the ingestible physiological monitor 100 can bypass the stomach 502, similarly or according to 304 of process 300. In some non-limiting examples, the enteric capsule can dissolve, releasing the ingestible physiological monitor in the compact shape 265 and into the intestines 504, similarly or according to 306 of process 300. In some non-limiting examples, the compact shape 265 can be released, allowing the ingestible physiological monitor 100 to unfold and adhere to the wall of the intestine 504, similarly or according to 308 of process 300. In some non-limiting examples, once the ingestible physiological monitor 100 has adhered to the intestine, the monitor can receive, analyze, and transmit physiological data, similarly or according to 310 of process 300. In some non-limiting examples, the ingestible physiological monitor 100 can reach a lifetime, disassemble, and be excreted passing through large intestine 506, similarly or according to 312 and/or 314 of process 300. In some non-limiting examples, 310 of process 300 can be completed at any time during process 300 (e.g., capturing, analyzing, and transmitting physiological data).

It should be noted that, as used herein, the term mechanism can encompass hardware, software, firmware, or any suitable combination thereof. It should be understood that the above described steps of the process of FIG. 7 can be executed or performed in any order or sequence not limited to the order and sequence shown and described in the figures. Also, some of the above steps of the process of FIG. 7 can be executed or performed substantially simultaneously where appropriate.

Although the invention has been described and illustrated in the foregoing illustrative non-limiting examples, it is understood that the present disclosure has been made only by way of example, and that numerous changes in the details of implementation of the invention can be made without departing from the spirit and scope of the invention, which is limited only by the claims that follow. Features of the disclosed non-limiting examples can be combined and rearranged in various ways.

What is claimed is:

1. An ingestible system configured to acquire physiological information from an interior of a subject, the system comprising:
   a substrate;
   at least one physiological sensor coupled to the substrate and configured to capture physiological data from a digestive tract of the subject, the at least one physiological sensor includes a first electrode and a second electrode;
   a controller coupled to the substrate and configured to receive the physiological data and prepare the physiological data for one of transmission from the subject or analysis of the physiological data; and
   wherein the substrate, with the at least one physiological sensor and the controller coupled thereto is configured to self-orient within the digestive tract of the subject during ingestion of the system by the subject to orient the at least one physiological sensor in the at least one of the internal area or the orientation in the digestive tract of the subject.

2. The system of claim 1 wherein the at least one physiological sensor and the controller are coupled on a common side of the substrate.

3. The system of claim 2 further comprising a mucoadhesive arranged on a side of the substrate that is opposite from the common side to couple the system to the at least one of the internal area or the orientation in the digestive tract of the subject after the substrate self-orients.

4. The system of claim 1 further comprising a communication circuit configured to receive the at least one of the physiological data or analyzed physiological data from the controller to communicate externally from the subject.

5. The system of claim 1 further comprising a housing surrounding the substrate, the at least one physiological sensor, and the controller.

6. The system of claim 5 wherein the housing includes a capsule that is configured to disintegrate after being subjected to the digestive tract.

7. The system of claim 6 wherein the substrate is adjustable between a folded position and an extended position and wherein the substrate is in the folded position within the capsule and moves to the extended position after the capsule decomposes to self-orient the substrate in the digestive tract.

8. The system of claim 1 wherein the at least one physiological sensor includes at least one of:
a first electrode, a second electrode, or a pulse generator, and wherein the pulse generator is configured to emit current pulses through the first or second electrode, to perform impedance measurements across the first electrode and the second electrode;
at least one of a first electrode and a second electrode configured to capture electrocardiogram signals;
a pulse oximeter configured to acquire an oxygen saturation measurements; or a temperature sensor configured to measure an internal temperature of the subject.

9. The system of claim 1 wherein the internal area includes an intestine of the subject.

10. The system of claim 1 further comprising an enteric coating covering the at least one physiological sensor and the controller to protect against an acidic pH environment and allows dissolving in a neutral pH environment.

11. The system of claim 1 wherein the at least one physiological sensor includes:
a first electrode, a second electrode, or a pulse generator, and wherein the pulse generator is configured to emit current pulses through the first or second electrode, to perform impedance measurements across the first electrode and the second electrode;
at least one of a first electrode and a second electrode configured to capture electrocardiogram signals;
a pulse oximeter configured to acquire an oxygen saturation measurements; and
a temperature sensor configured to measure an internal temperature of the subject.

12. The system of claim 1 wherein the at least one physiological sensor includes:
a pulse oximeter in communication with the controller for capturing a blood oxygenation parameter or a respiration signal; and
an electrocardiogram in communication with the controller for capturing an electrical signal of a heart.

13. The system of claim 12, wherein the at least one physiological sensor further comprises:
a first electrode, a second electrode, or a pulse generator, and wherein the pulse generator is configured to emit current pulses through the first or second electrode, to perform impedance measurements across the first electrode and the second electrode; and
the first electrode and the second electrode in electrical communication with the electrocardiogram.

14. The system of claim 1 wherein the substrate includes a plurality of mechanical links integrally formed in the substrate, the mechanical links separating at least one of the controller, and the at least one physiological sensors.

15. The system of claim 14 wherein the mechanical links comprise a biogalvanic material electrically connected to the controller, the controller executing at least a portion of a computer program to cause the mechanic links to degrade.

16. A method for internal monitoring, the method comprising:
ingesting an ingestible system, the ingestible system comprising a capsule and a physiological monitor, the physiological monitor comprising:
a substrate;
at least one physiological sensor coupled to the substrate;
a controller coupled to the substrate and configured to receive physiological data and prepare the physiological data for one of transmission from a subject or analysis of the physiological data;
wherein the substrate of the physiological monitor is folded, such that the physiological monitor is bent over itself so that one part of the physiological monitor covers another part of the physiological monitor thereby creating a folded physiological monitor that is placed in the capsule to be ingested by a subject;
dissolving the capsule in a portion of an intestine of the subject to release the folded physiological monitor in the portion of the intestine; and
unfolding the folded physiological monitor in the portion of the intestine.

17. The method of claim 16 further comprising self-orienting the physiological monitor in the portion of the intestine, such that a first surface of the physiological monitor faces a wall of the portion of the intestine.

18. The method of claim 16, wherein a first surface of the physiological monitor includes a mucoadhesive, and further comprising adhering the first surface of the physiological monitor to the wall of the portion of the intestine.

19. The method of claim 16 further comprising the controller transmitting an alert to an external device, based on a physiological parameter.

20. The method of claim 16 wherein the physiological monitor further comprises:
a first electrode, a second electrode, or a pulse generator, and wherein the pulse generator is configured to emit current pulses through the first or second electrode, to perform impedance measurements across the first electrode and the second electrode;
at least one of a first electrode and a second electrode configured to capture electrocardiogram signals;
a pulse oximeter configured to acquire an oxygen saturation measurements; and
a temperature sensor configured to measure an internal temperature of the subject.

21. The method of claim 20 wherein an impedance waveform is generated from the impedance measurements, the impedance waveform indicating a respiratory signal.

22. The method of claim 16 wherein the capsule includes an enteric coating, such that when the capsule is ingested, the capsule remains stable in an acidic pH environment, and the capsule dissolving in a neutral pH environment.

23. An ingestible system comprising:
- a substrate; and
- a physiological sensor coupled to the substrate, the physiological sensor being at least one of a pair of electrodes, or a pulse oximeter;
- wherein the ingestible system is configured to adhere to a lining of an intestine of a subject when the ingestible system contacts the lining of the intestine of the subject; and
- wherein when the ingestible system is adhered to the lining of the intestine of the subject, the physiological sensor is configured to capture physiological data of the subject, the physiological data including at least one of an ECG signal, an impedance signal, a respiratory signal, or a blood oxygenation parameter.

24. The ingestible system of claim 23, wherein the substrate is flexible and is planar.

25. The ingestible system of claim 23, further comprising a controller coupled to the substrate, the controller being configured to:
- receive, from the physiological sensor, the physiological data; and
- transmit the physiological data to an external device.

\* \* \* \* \*

UNITED STATES PATENT AND TRADEMARK OFFICE
CERTIFICATE OF CORRECTION

| | |
|---|---|
| PATENT NO. | : 11,690,550 B2 |
| APPLICATION NO. | : 16/633100 |
| DATED | : July 4, 2023 |
| INVENTOR(S) | : Jeremy Ruskin et al. |

It is certified that error appears in the above-identified patent and that said Letters Patent is hereby corrected as shown below:

In the Specification

Column 1, Lines 7-10:
"This application is based on, claims the benefit of, and claims priority to U.S. Provisional Application No. 62/537, 137, filed Jul. 26, 2017, which is hereby incorporated by reference herein in its entirety for all purposes."

Should be:
--This application is a U.S. National Phase of PCT Application No. PCT/US2018/043925 filed on July 26, 2018, which is based on, claims the benefit of, and claims priority to U.S. Provisional Application No. 62/537,137, filed July 26, 2017, the entire contents of all of these applications are incorporated herein by reference in their entirety for all purposes.--

Signed and Sealed this
Nineteenth Day of September, 2023

Katherine Kelly Vidal
*Director of the United States Patent and Trademark Office*